United States Patent [19]

Robbat, Jr. Albert et al.

[11] Patent Number: 4,801,430

[45] Date of Patent: Jan. 31, 1989

[54] INTERFACE FOR SEPARATING AN ANALYTE OF INTEREST FROM A LIQUID SOLVENT

[75] Inventors: Robbat, Jr. Albert, Tewksbury; Nicholas P. Corso, Watertown, both of Mass.

[73] Assignee: Trustees of Tufts College, Medford, Mass.

[21] Appl. No.: 911,350

[22] Filed: Sep. 25, 1986

[51] Int. Cl.⁴ .............................................. B01D 49/00
[52] U.S. Cl. ...................................... 422/52; 422/54; 422/70; 422/89; 422/90; 422/101; 422/103; 436/161; 250/288; 250/289
[58] Field of Search .................. 422/70, 89, 101, 103, 422/52, 54, 90; 436/161; 73/23.1, 61.1 C; 210/656; 250/288 A, 289

[56] References Cited

U.S. PATENT DOCUMENTS

| | | | |
|---|---|---|---|
| 3,967,931 | 7/1976 | Juvet, Jr. et al. | 422/70 X |
| 4,055,987 | 11/1977 | McFadden | 422/70 X |
| 4,066,409 | 1/1978 | Fine | 422/70 X |
| 4,552,723 | 11/1985 | Adams et al. | 422/70 X |
| 4,600,559 | 7/1986 | Hiatt | 422/89 |

Primary Examiner—Michael S. Marcus
Assistant Examiner—Jill Johnston
Attorney, Agent, or Firm—David Prashker

[57] ABSTRACT

An interface generally useful for liquid chromatography systems and methods is provided for the separation of an analyte of interest from a liquid solvent. The interface provides for separation and collection of solvent and the analyte of interest in a gaseous molecular state. In this manner, the ability to detect, identify, and quantify the analyte of interest using a variety of specific and non-specific detectors is made possible.

16 Claims, 5 Drawing Sheets

1) NITROBENZENE
2) 1,8-DINITRONAPTHALENE
3) 1,5-DINITRONAPTHALENE
4) 1-NITRONAPTHALENE
5) 1-NITRO-2-METHYLNAPTHALENE
6) 3-NITROBIPHENYL
7) 9-NITROANTHRACENE
8) 3-NITROFLUORANTHENE
9) 6-NITROCHRYSENE

INTERFACE FOR SEPARATING AN ANALYTE OF INTEREST FROM A LIQUID SOLVENT

FIELD OF THE INVENTION

The present invention is concerned with apparatus for advantageously combining liquid chromatography separation systems and equipment with gas chromatography detection systems and assemblies, and is particularly directed to interfaces for separating an analyte of interest from a liquid solvent carrier for subsequent analyses by any detector without the need of liquid chromatography methods and assemblies.

BACKGROUND OF THE INVENTION

The science of material separation has undergone explosive growth as scientists and engineers have taken advantage of physical and chemical phenomena to separate the components of a mixture and developed analytical separation processes for a variety of applications. These developments include chromatographic methods, ultrafiltration techniques, electrophoresis and the like. A specialized branch of separation science comprises gas and liquid chromatographies. Gas chromatography (hereinafter "GC") separates components, solutes, in a complex mixture by partitioning the solute between a gaseous mobile phase and a liquid or solid stationary phase. Gas chromatography is an ideal separation technique for thermally stable, low molecular weight organic compounds between 50-250 daltons in complex mixtures. Since a mobile inert gas is used to carry the solute(s) through the apparatus, many more analytical detectors and detection techniques are amenable to gas chromatography than in liquid column chromatography. On the other hand, liquid chromatography (hereinafter "LC") is the separation of solutes based upon partitioning between two immisible liquid phases, one stationary and the other mobile, or between a liquid mobile phase and a stationary solid phase. High Performance Liquid Chromatography (hereinafter "HPLC") has been developed to decrease the time of analysis over LC and has found wide use as both analytical and preparative separation tools.

One major disadvantage of HPLC and LC in comparison to GC techniques is the limited number of available detectors and detection methodologies, particularly with respect to detection of one or more specific analytes. To overcome this obstacle, a variety of means for combining gas chromatography detectors with HPLC assemblies have been devised. Exemplifying these efforts are the innovations described in U.S. Pat. Nos. 3,835,332; 3,877,875; 3,973,910; 3,996,002; 3,996,003; 3,996,004; 3,996,008; 3,996,009; 4,066,409; and 4,070,155.

Despite such innovations, there remains a recurring series of obstacles, disadvantages, and problems in known apparatus developed in an effort to integrate and combine liquid chromatography systems with gas chromatography detectors. For example, a continuing inability to detect an analyte of interest exists because the liquid solvent carrier is not adequately or effectively separated from the analyte of interest, such that, at the time of detection, there is a concomitant inability to identify and accurately measure the analyte in the sample. Furthermore, the inability to separate the liquid solvent from the analyte prior to detection causes major losses of sensitivity and specificity. It is clear, therefore, that there remains a continuing and recognized need for specific apparatus which is effective and reliable for the separation of at least one analyte of interest from a liquid solvent carrier.

SUMMARY OF THE INVENTION

The present invention provides an interface for separating an analyte of interest from a liquid solvent carrier comprising: conduit means for conveying a liquid solvent carrying at least one analyte of interest as a solute; means for vaporizing the liquid solvent and the analyte of interest into a dry gaseous mixture; an expansion chamber under reduced pressure for adiabatic expansion of the dry gaseous mixture whereby the dry gaseous mixture becomes separated into gaseous solvent molecules migrating substantially toward the internal periphery of the expansion chamber and into gaseous analyte molecules migrating substantially toward the internal center of the expansion chamber; solvent gas collection means at the internal periphery of the expansion chamber for collecting said gaseous solvent molecules; and analyte gas collection means at the internal center of the expansion chamber for collecting the gaseous analyte molecules.

DETAILED DESCRIPTION OF THE FIGURES

The present invention may be more completely and easily understood when taken in conjunction with the accompanying drawing, in which.

Figure 4:
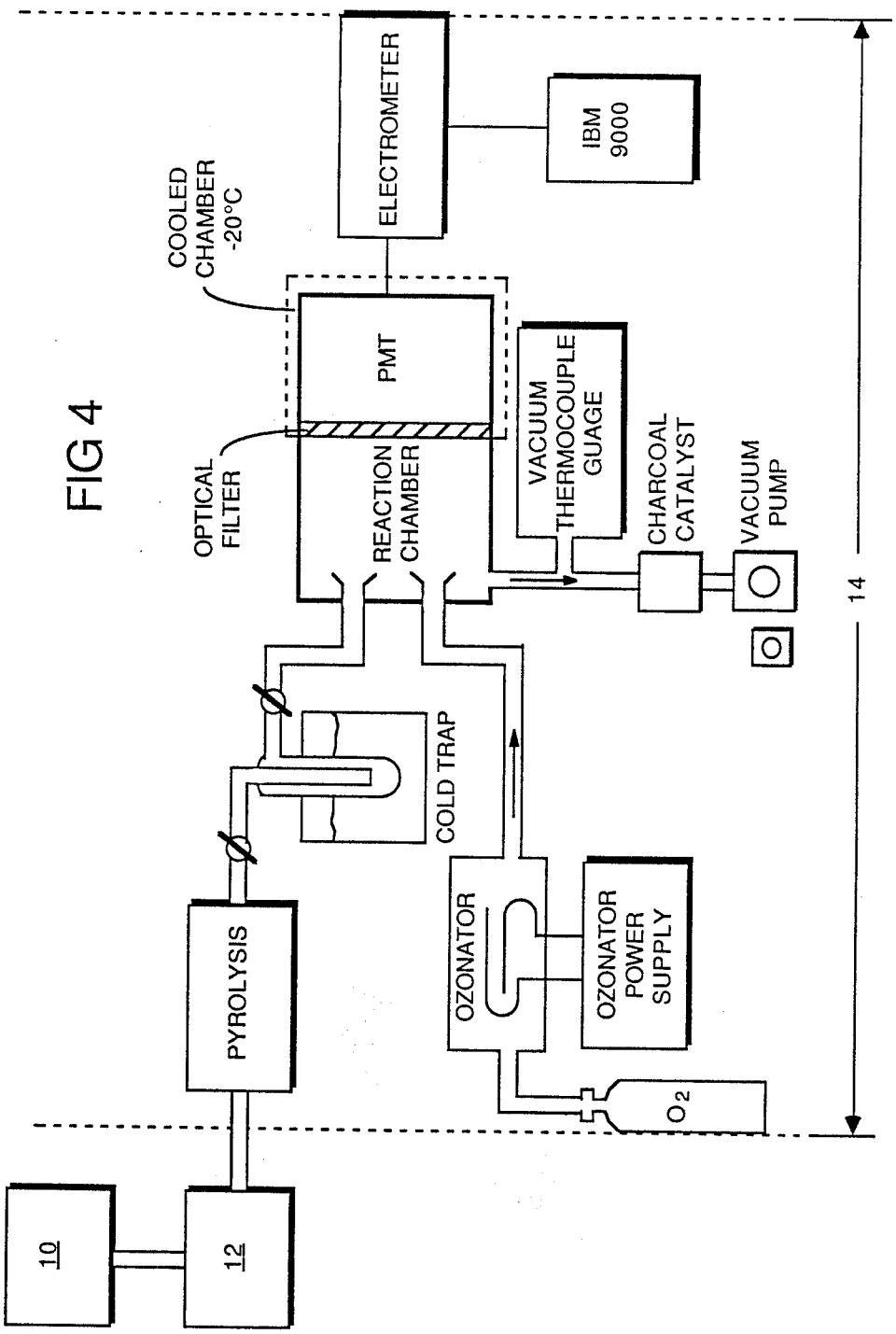
Figure 5:
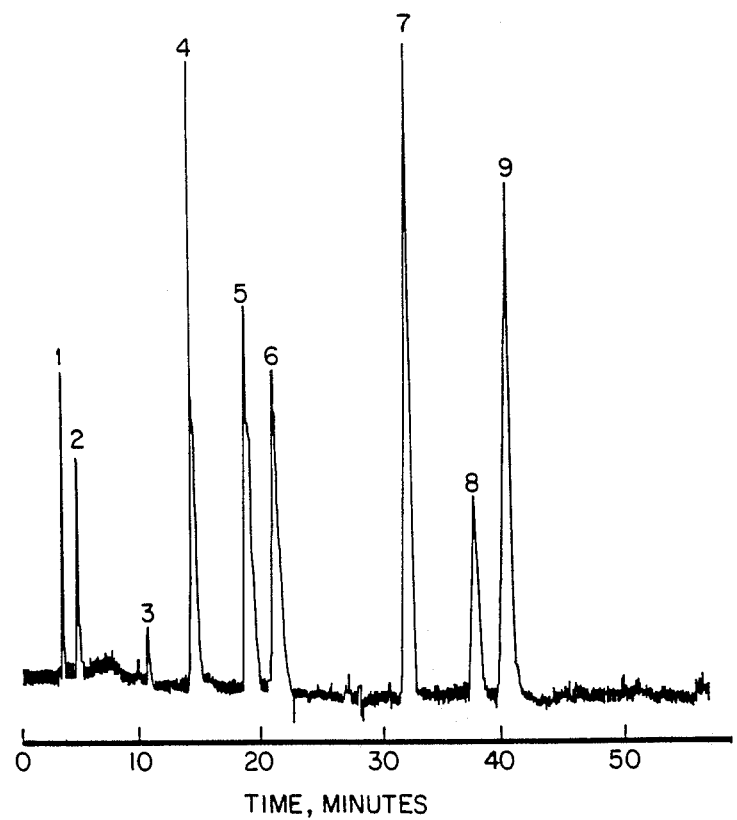

FIG. 4 is a schematic illustration of a thermal vaporization interface positioned between a high pressure liquid chromatography system and a gas chromatographic chemiluminescent detection system for the analysis of nitrated polycyclic aromatic hydrocarbons; and FIG. 5 is a chromatographic profile of detected nitrated polycyclic aromatic hydrocarbons separated from a liquid solvent utilizing the interface of the present invention.

DETAILED DESCRIPTION OF THE PREFERRED EMBODIMENTS

The present invention is an interface generally applicable to all separation systems in which a liquid admixture can be vaporized into a dry, gaseous state without decomposition or fragmentation, and is particularly applicable to liquid chromatography (hereinafter "LC") systems which employ specific and non-specific detectors and detection assemblies in which the solvent effluent is known to interfere with the measurement of an analyte of interest in the sample or to cause direct interference with the detector assembly. The ability to accurately and precisely measure an analyte of interest in a solvent carrier relies upon the ability of the detector to identify and measure at least one parameter indicative of the analyte alone. The presence of this parameter and the ability to distinguish this parameter or signal in the presence of other substances determines the specificity, selectivity and sensitivity of the detector and detection assembly. As an illustrative example, the liquids conventionally used as solvents in LC which employ chemiluminescent detection apparatus quench the signal and severely limit the sensitivity and thus the response of the detector, as well as the detection system as a whole. Moreover, solvents containing water and organic solvents having high thruput in LC systems generally eliminate the usefulness of flame ionization, NIP, and mass spectrometric detectors as well.

The present invention may be advantageously employed as a general interface for the separation of at least one analyte of interest from a liquid solvent; and to enhance and improve the accuracy and sensitivity of detectors and detection methods generally without regard as to whether or not a LC assembly is utilized. The interface allows the user to employ flame ionization detectors; electron capture detectors; N/P-specific detectors; sulfur specific detectors; thermionic ionization detectors; and all other detectors and detection assembly useful in analytical or preparative separation chemistry in which the solvent carrier would otherwise interfere with the signal or parameter indicative of the analyte of interest.

Figure 1:
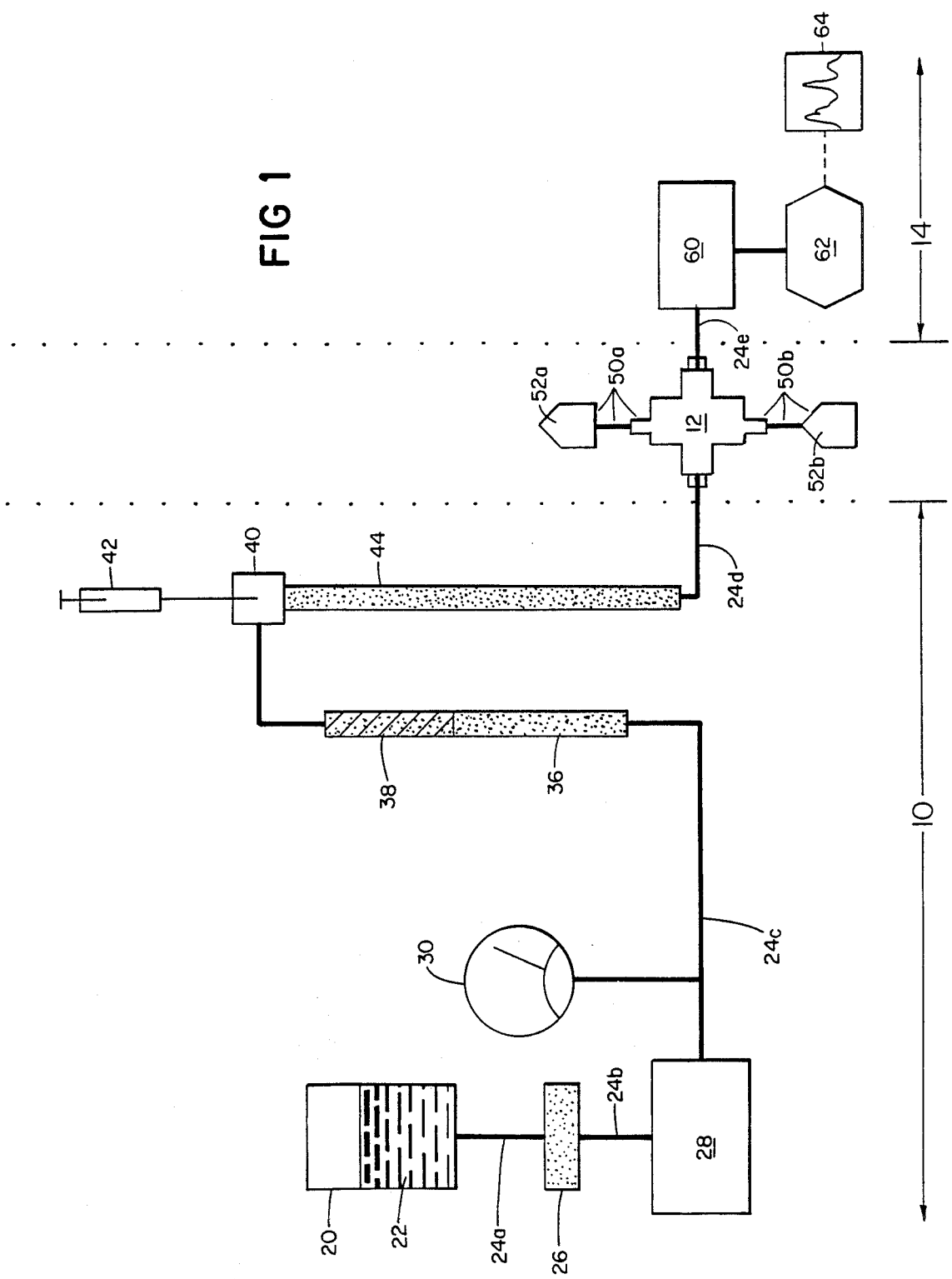
FIG. 1 is a schematic illustration of a conventional liquid chromatography assembly employing the interface of the present invention.

Demonstrating merely one application for the present invention is the general instrumentation seen in FIG. 1 which illustrates the use of a liquid column chromatography system or a high pressure liquid chromatography system in combination with a gas chromatography detection system. The LC portion 10 is in direct flow communication with the GC detector portion 14 via the interface 12, which, in combination, forms the entirety of the instrumentation system 8 useful for analytical and preparative purposes generally. The LC portion 10 includes a solvent reservoir for the mobile phase 20 which contains a quantity of prepared liquid solvent 22. The solvent 22 may comprise an organic liquid; a blend of different organic liquids; water; or a blend of water and one or more organic liquids as conventionally known in this art. The liquid solvent 22 serves as a carrier or eluent throughout the entirety of the LC portion 10 of the instrumentation 8 and is directed to each of the components via a series of conduits 24 which convey the solvent from one part of the system to another. Initially, solvent 22, from which all gases have been removed, is carried by the conduit 24a through a filter 26 to ensure removal of all sediment or other particles. Subsequently, the filtered solvent is carried by conduit 24b to a pump 28 which may be a reciprocating pump, a syringe-type pump, a constant-pressure pump, or any other pump conventionally known in this art. The solvent pump, typically equipped with a damping unit to minimize pulsating action and a pressure guage 30, forces the liquid solvent (the mobile phase) under pressure through the conduit 24c. If needed or desired, the liquid solvent 22 is carried via the conduit 24c to an optional precolumn 36 which presaturates the solvent comprising the mobile phase with a chosen stationary phase material and an optional guard column 38 which prevents contamination of the solvent prior to its combination with a test sample. Typically, however, the saturated liquid solvent 22 is carried via conduit 24c directly to an injection head 40 which permits introduction of a test sample into the column via a syringe-septum injection means 42 or a series of conventionally known sampling valves and loops (not shown). The test sample containing the analyte of interest is admixed with the liquid solvent within the injection head 40 and the formed admixture introduce directly into a separation of analytical column of various composition and design conventionally known in this art. The liquid solvent 22 and analyte of interest emerges from the separation column 44 as a liquid effluent mixture via the conduit 24d and is directed to the interface 12 comprising the present invention.

The interface 12 serves to separate the solvent from the analyte of interest and collects each independently after separation. The solvent 22 is drawn out of the interface 12 in gaseous form under vacuum via solvent gas collection means 50a, and 50b and is typically stored in liquid form in solvent retaining chambers 52a and 52b respectively. The separated analyte of interest exits the interface 12 via conduit 24e in gaseous form and is carried to the GC detector portion 14 of the instrumentation 8. Typically, the GC detector portion 14 includes an assembly 60 for physical and chemical manipulation of the analyte of interest such that the detector 62 will identify and accurately measure the analyte with subsequent recording of the detection results in the form of a chromatographic profile 64.

As customary, the components of the manipulative assembly 60 and the choice of detector 62 will vary with the nature of the analyte of interest to be measured and the convenience and/or personal preference of the user from among those readily available commercially are known in the literature. The choice of detector 62 thus include all known thermal conductivity detectors, flame ionization detectors, thermionic emission detectors, flame photometric detectors, electron capture detectors, helium detectors, photoionization detectors, and the like conventionally known and used in this art. Merely illustrative of a useful GC detector portion 14 is the chemiluminescent detection system of FIG. 4 in which the manipulative assembly includes a combination of pyrolysis chambers, cold traps, reaction chambers, vacuum pumps, thermocouples, catalysts and other apparatus specially designed to meet the requirements of a chemiluminescent detector.

Figure 2:
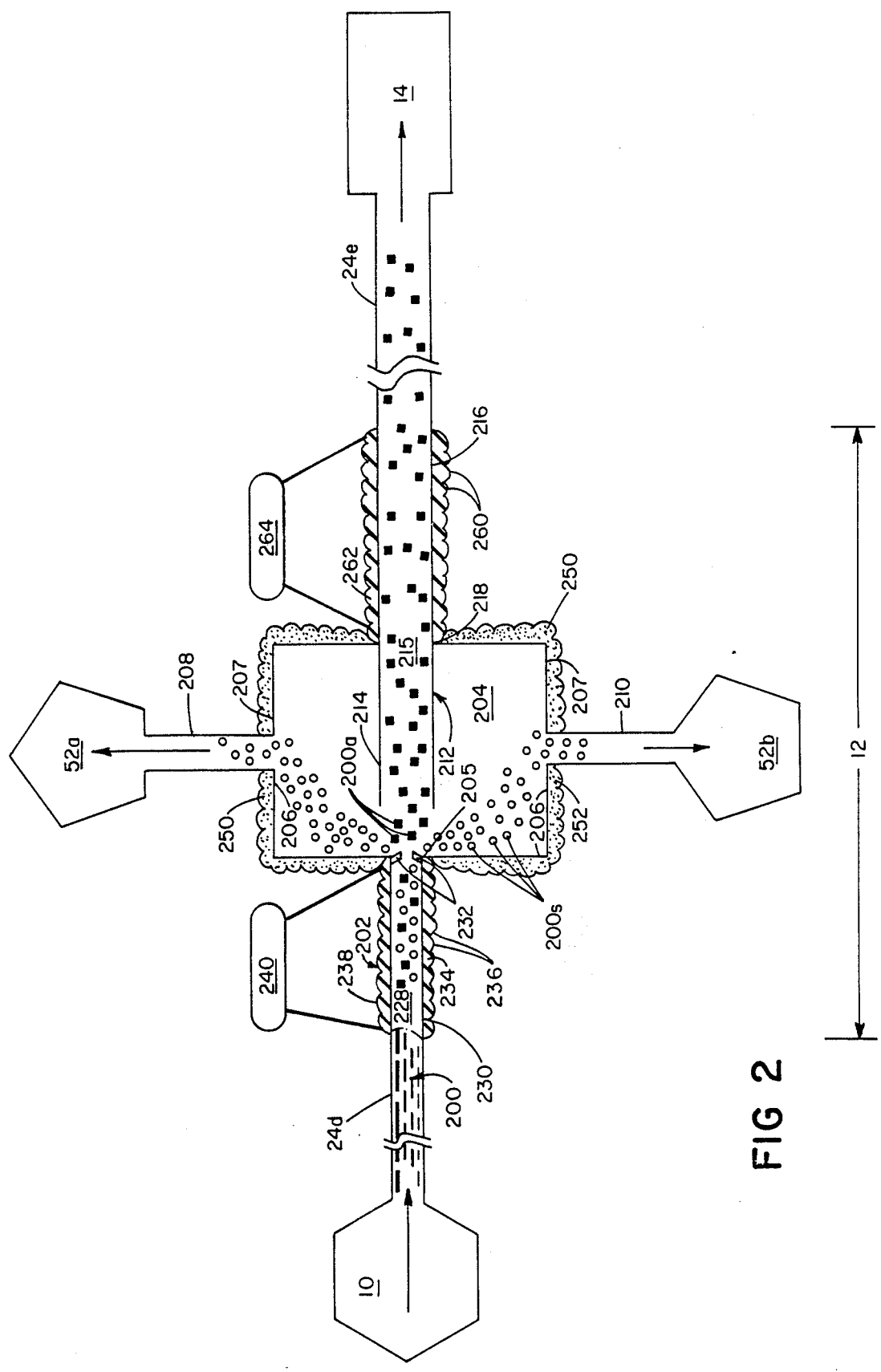
FIG. 2 is a detailed cross-sectional view of the preferred thermal vaporization interface comprising the present invention.
Figure 3:
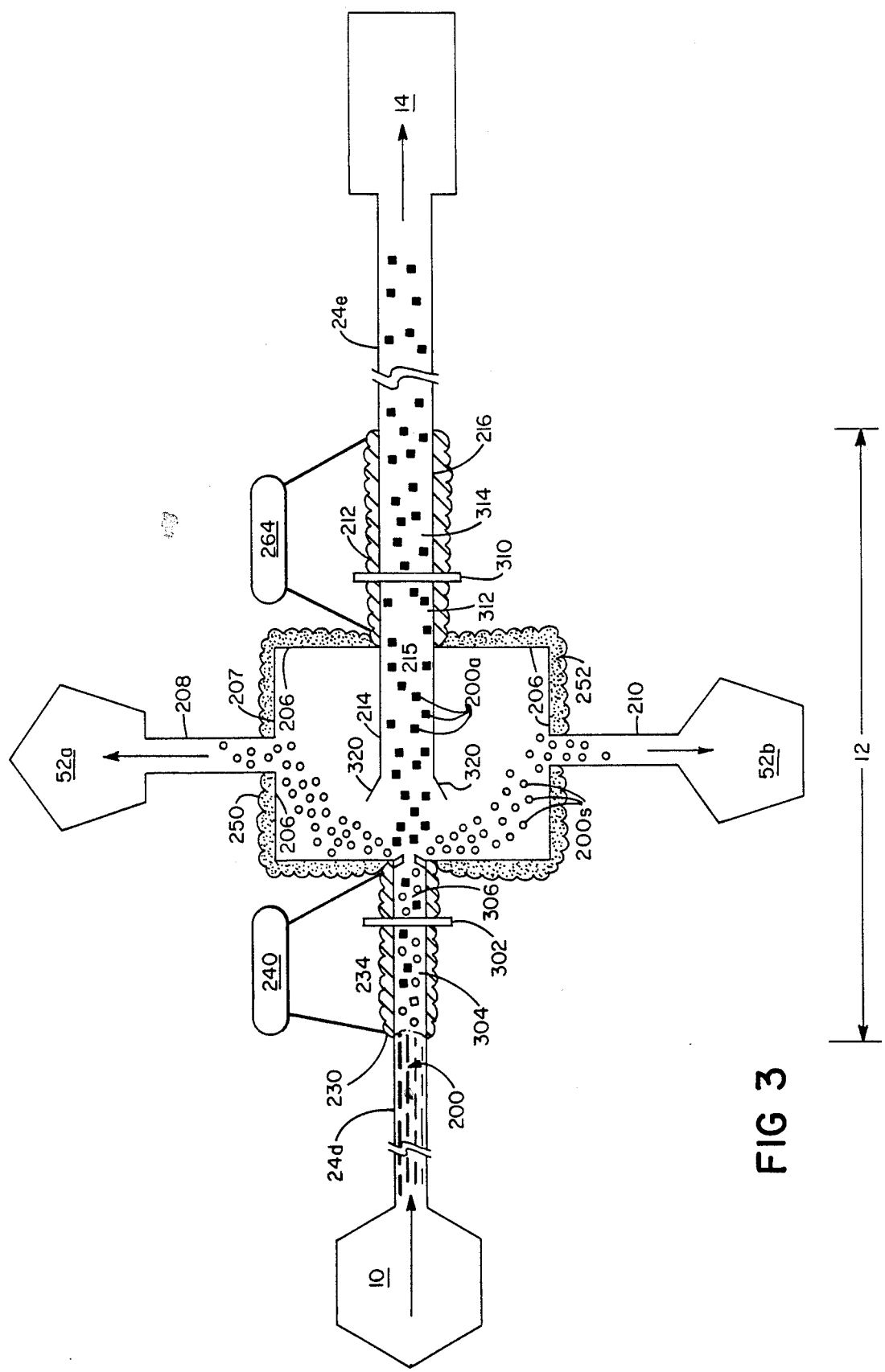
FIG. 3 is a cross-sectional view of another preferred embodiment comprising the thermal vaporization interface of the present invention.

Preferred embodiments of the interface 12 comprising the present invention are illustrated by FIGS. 2 and 3 respectively. As seen in FIG. 2 the interface 12 comprises liquid vaporizing means 202; an expansion chamber 204; solvent gas collection means 50a and 50b; and analyte gas collection means 214. The liquid effluent mixture 200 comprising a liquid solvent carrier of choice and at least one analyte of interest is introduced into the interface 12 via the conduit 24d which is in fluid communication with the vaporizing means, the liquid vaporization arm 202. The vaporization arm 202 is joined to an expansion chamber 204 maintained under reduced (vacuum) pressure. At the internal periphery 206 of the expansion chamber 204 are joined a plurality of solvent gas collection means 50a and 50b comprising solvent gas collection tubes 208, 210 and a vacuum pressure source (not shown). The solvent collection tubes 208, 210 are maintained under reduced pressure (vacuum) and are individually joined to and in fluid communication with solvent retaining chambers 52a and 52b for retention of collected solvent. Centrally disposed within the interior of the expansion chamber 204 are analyte gas collection means 212 comprising at least one analyte gas collection tube 214 maintained under reduced pressure and extending through the center of the expansion chamber 204. One end of the analyte gas collection tube 214 is positioned in the proximity of the juncture 205 between the liquid vaporization arm 202 and the expansion chamber 204. The other end of the analyte gas collection tube 214 extends to and merges with an analyte outlet arm 216 maintained under vacuum pressure which is in fluid communication with conduit 24e leading to the GC detector portion 14.

The liquid vaporization arm 202 comprises an inlet tube 230 and means for vaporizing a liquid admixture of a liquid solvent and an analyte of interest 234. The inlet tube 230 is formed of a chemically neutral and resilient material such as stainless steel and is preferably threaded for precise placement of the tubing within the vaporization arm. The inlet tube 230 may be of any diameter and thickness compatible with analytical, preparative, and microbe LC systems and is joined to the conduit 24d using conventional means to prevent leakage of fluid. Preferably, the end of the inlet tube 230 at the juncture 205 with the expansion chamber 204 is inwardly beveled to form a nozzle 232, the exact nozzle configuration varying with the type of LC system employed. Alternatively, the end of the inlet tube 230 at the juncture 205 may be linear without any inward or outward bevel whatsoever. Surrounding the exterior surface and preferably coextensive with the axial length of the inlet tubing 230 are vaporization means 234 preferably comprising a series of heating coils 236 imbedded in an insulating material layer 238. The heating coils 236 are in electrical communication with a source of electrical energy 240 which serves to heat the coils within the insulating material layer 238 and to maintain the interior spatial volume 228 of the inlet tube 230 at a preselected temperature ranging from 100°-700° C. While electrical heating means are most preferred, alternative means for heating and maintaining the interior spatial volume 228 at a preselected temperature are conventionally known and may be substituted freely at will.

The expansion chamber 204 is composed of a pressure resistant and heat conductive material which can be varied in dimensions and configuration to meet the user's needs or convenience. Disposed upon the external surface 207 of the expansion chamber 204 is an insulating layer 250 which preferably includes expansion chamber heating means 252 of conventionally known form such that the interior of the expansion chamber 204 is maintained at a preselected temperature ranging from 100°-700° C.

The solvent gas collection tubes 208, 210 are in fluid communication with the internal periphery 206 of the expansion chamber 204 and the solvent retaining chambers 52a and 52b. The vacuum pressure source maintains each tube 208, 210 at a reduced pressure ranging from 1-100 and preferably from 1-50 micron. The dimensions, internal diameter, composition, and mode of attachment of the solvent gas collection tubes is that conventionally used in the art.

The analyte gas collection means 212 comprises the gas collection tube 214 and the outlet arm 216 which extends from the expansion chamber 204 at the juncture 218. Surrounding the exterior surface of the outlet arm 216 are preferably a second set of heating coils 260 embedded in an insulating material layer 262 which are in electrical communication with a source of electrical energy 264. The combination of the heating coils 260 with the insulating material layer 262 serves as heating means to maintain the internal volume 215 of the outlet arm 216 at a preselected temperature ranging from 100°-700° C. In addition, a source of vacuum (not shown) is provided such that the analyte catch tube 214 and the outlet arm 216 are maintained under a reduced pressure ranging from 1-100 and preferably from 1-50 microns of mercury. Subsequently, the outlet arm 216 engages and is continuous with the conduit 24e which directs the separated gas molecules comprising the analyte of interest to the GC detection system 14.

The interface illustrated in FIG. 2 serves to separate an analyte of interest from a liquid solvent in admixture in the following manner: the liquid admixture 200 comprising liquid solvent and at least one analyte (solute) of interest is introduced as a liquid into the liquid vaporization arm 202 via the inlet tubing 230. The vaporization means 234 comprising heating coils 236, the insulating material layer 238 and the electrical energy source 240 maintain the internal spatial volume 228 at an elevated temperature sufficient to cause vaporization of the liquid admixture into gaseous molecules of solvent 200s (illustrated as small open circles) and gaseous molecules of the analyte of interest 200a (illustrated as small darkened squares). The interior spatial volume 228 of the inlet tube 230 is maintained at an elevated temperature which is controlled and monitored to be less than that temperature at which decomposition or fragmentation of the solvent and/or analyte of interest occurs; concomitantly, the internal temperature is maintained at a level greater than that required to vaporize both the solvent and the analyte of interest in the admixture and to maintain each of them individually in the gaseous state as a vapor. Such temperatures range from 100°-700° C. but preferably are maintained at a level between 100°-400° C. in most instances.

Two distinct situations will occur directly as a result of vaporizing the liquid admixture with the vaporization arm 202. If the solvent leaving the LC system contains some meaningful proportion of water (typically greater than 1.0% by volume), the vaporization of the liquid admixture will result in the formation of a wet vapor comprising gaseous molecules of the analyte of interest; gaseous molecules of the organic solvent; and a suspension of fine, liquid droplets of water carried by the gaseous molecules. The wet vapor upon exiting the vaporization arm 202 and entering the expansion chamber 204 undergoes adiabatic expansion and will form a wet aerosol. Upon continued heating, the liquid water droplets of the aerosol will vaporize forming gaseous molecules in a dry state and the aerosol becomes a completely dry gaseous admixture. The expansion chamber 204, being at a preselected temperature ranging from 100°-700° C. and at a reduced pressure, will maintain all the components of the vaporized admixture in a dry gaseous state.

Alternatively, if the solvent 22 comprises comparably little or no water (typically from 0-1.0% by volume), the liquid admixture 200 is vaporized directly within the liquid vaporization arm 202 into a dry gaseous mixture; is drawn into the interior of the expansion chamber 204; and undergoes adiabatic expansion as a dry mixture of gaseous molecules comprising the solvent 200s and gaseous molecules of the analyte of interest 200a. The elevated temperature within the expansion chamber 204 then maintains the respective molecules of solvent and analyte in a completely gaseous state.

In all instances, the adiabatic expansion of the admixture within the expansion chamber causes the separation of its consituents. The gaseous molecules of solvent 200s, being generally of low molecular weight (typically less than 100 daltons) are directed toward the internal periphery 206 of the expansion chamber and encounter the solvent gas collection tubes 208, 210 which are under vacuum pressure of 1-50 microns. The gaseous molecules of solvent 200s are drawn into the collecton tubes 208 and 210 and removed to solvent retention chambers 52a and 52b where they are maintained in liquid form. Concurrently the gaseous molecules comprising the analyte of interest 200a, being generally greater in molecular weight than the corresponding gaseous molecules of solvent (typically more than 100 daltons), become directed toward the internal center of the expansion chamber. The gaseous molecules of analyte migrating to the approximate internal center of the expansion chamber encounter the analyte gas collection tube 214 and are drawn into its interior spatial volume 215 via the vacuum pressure maintained within the collection tube. The gaseous molecules comprising the analyte of interest 200a are then drawn through the interior spatial volume 215 of the collection tube 214 into the heated interior of the outlet tube 216 which maintains them in a gaseous state. The collected analyte gas molecules are then directed into the conduit 24e for detection via the GC detection assembly 14.

Another preferred embodiment of the interface comprising the present invention is provided by FIG. 3 which is similar to that of FIG. 2 and further comprises a plurality of porous, semi-permeable membranes. As is seen in FIG. 3, a first membrane 302 is disposed within the liquid vaporization arm 202 and completely transects the inlet tube 230 such that the internal spatial volume 228 is divided into two distinct spaces 304 and 306 respectively. The remainder of the vaporization arm is as has been described previously for FIG. 2. A second membrane 310 is disposed within and completely transects the analyte outlet arm 216 into two internal spaces 312 and 314. The function of the membranes 302 and 310 respectively is to: ensure that the gaseous molecules passing through the membrane are completely dry and to selectively prevent liquid or wet material (in the form of droplets, particles, suspensions, colloids and the like) from passing into the expansion chamber 204; and to prevent subsequent collection of gaseous molecules of analyte which are not completely dry. Membranes which selectively prevent the passage of liquid or wet compositions are exemplified by tetra-fluroethylene membranes, commercially available as hydrophobic Durophore and Fluoropore membranes; are of varying pore size and porosity to meet specific requirements; and are commercially available in a variety of formats for such purposes. The membranes may be disposed within housing chambers which prevent bending, tearing, or rupture of the membrane due to the vacuum forces, the temperature, or the volume of the admixture being separated.

An added feature visible in the embodiment of FIG. 3 is the design of the analyte gas collection tube 214 which extends substantially into the central interior of the expansion chamber 204. The end of the collection tube 214 in the proximity of the juncture 205 is formed as an outwardly extending bevel 320 which is advantageous in capturing the gaseous molecules of analyte as they separate and migrate during adiabatic expansion within the chamber 204. All other features are as previously described for the embodiment illustrated by FIG. 2.

While the preferred embodiments of the interface comprising the present invention are as described above, the individual investigator or user will vary certain features and operating parameters to meet specific non-chromatographic and chromatographic applications and analyses. Some features become particularly advantageous when the interface is utilized for analytical or small scale systems in comparison to preparative or large scale systems. These include:

(1) The operating temperatures within the liquid vaporization arm, the expansion chamber, and the analyte outlet arm: In general, the operating temperatures of the liquid vaporization arm, the expansion chamber and the analyte outlet arm are kept at a single uniform level which will be preselected in accordance with the characteristics of the analyte of interest and the characteristics of the solvent. For most applications an operating temperature of 300°–400° C. provides optimal results. If a variance in temperature between different parts of the interface are deemed useful, it is expected that the temperature of the liquid vaporization arm will be less than the temperature within the expansion chamber; which, in turn, will be less than the temperature within the analyte outlet arm.

(2) The diameter of the inlet tube in the liquid vaporization arm: In general, the diameter of the inlet tube should be smaller than the internal volume of the expansion chamber and smaller than the internal diameter of the analyte gas collection tube centrally disposed within the expansion chamber. In most instances, it is preferred that the inlet tube contain an inwardly beveled edge to form a nozzle at the juncture with the expansion chamber. The diameter of the opening at the nozzle will vary directly with the volume of the admixture; the reduced pressure within the expansion chamber; and is consistent with the type of chromatography being performed.

(3) The vacuum or reduced pressure within the expansion chamber is preferably equal or substantially similar to the vacuum pressure within the analyte gas collection tube and the vacuum pressure of the solvent gas collection tubes positioned along the internal periphery of the expansion chamber. Although a range from 1–100 micron is deemed useful, a working range of from 30–50 micron is deemed optimal.

(4) The end of the analyte collection tube at the central interior of the expansion chamber is preferably outwardly beveled to obtain most advantageous results in anaytical or small scale systems. In preparative and large scale systems, the large volume of admixtures to be separated by the interface permit the use of non-beveled analyte gas collection tubes.

(5) The comparative molecular weight (daltons) between the solvent and the analyte of interest will in major part dictate many of the operating features such as vacuum pressure gas, collection tube diameter, and the like. For example, where the solvent is considerably less than 100 daltons in molecular weight and the analyte of interest is comparably heavy (over 500 daltons) in molecular weight, the vaporization of these constituents in admixture into a dry gaseous mixture with subsequent release and expansion into a heated expansion chamber will result in a complete separation of gaseous solvent and gaseous analyte molecules. On the other hand, where there is little molecular weight difference between the solvent and the analyte, the particular operating parameters (heat, temperature, distance) and the specific design features (tube diameter, presence or absence of nozzles, and comparative sizes) become more critical for a complete and effective separation of constituents.

It will be appreciated that the interface comprising the present invention is useful in and for a variety of purposes and applications: these include preparative and analytical scale high pressure liquid chromatography; inclusion in systems employing atomic absorption, emission and fluorescence spectroscopy; inductively coupled plasma spectroscopy; mass spectroscopy; and any other non-chromatographic application where the constituents comprising a liquid admixture are able to be vaporized into a gaseous state and the separation of solvent from an analyte of interest is desired.

To illustrate both the utility and the effectiveness with which the interface comprising the present invention may be utilized in a specific application to detect and quantitatively measure one analyte of interest, the following example is provided. It will be expressly understood, however, that the specific example which follows is merely one illustration of the many chromatographic and non-chromatographic applications and variety of circumstances in which the present invention may be employed to advantage; the example provided is not, under any circumstances, to be deemed or viewed as limiting the invention to the described chromatographic analysis.

Analysis of Nitrated Polycyclic Aromatic Hydrocarbons

Nitrated polycyclic aromatic hydrocarbons (hereinafter "nitro-PAH") are reported to be among the most mutagenic compounds known and have produced cancer in laboratory animals. High Pressure Liquid Chromatography separates analytes of interest based upon competitive analyte partitioning between mobile and stationary phases. The more time the analyte spends in the stationary phase, the longer it takes for the analyte to elute from the chromatography column. If it can be separated from the liquid solvent carrier, nitro-PAH individually and as a class can be detected selectively from complex environmental samples using a gas chromatography chemiluminescent detection system [Robbat et al. *Anal. Chem.* 58: 2078 (1986)] using the assembly of FIG. 4.

The HPLC/interface/chemiluminescent detector (hereinafter "CD") system illustrated by FIG. 4 operates in the following manner: high pressure liquid chromatography (HPLC) of nitro-PAH containing samples can be achieved using the isocratic/gradient, normal phase or reverse phase modes. FIG. 4 illustrates the chromatography of nitro-PAH in the reverse phase mode using an acetonitrile/water liquid solvent as the mobile phase. The HPLC system 10 comprises a seven minute isocratic run of solvent 45/55% by volume followed by a 60 minute gradient period in which the solvent/mobile phase composition is changed to 75/25% by volume. The mobile phase flow rate is 300 ul/minute through a narrow bore $C_{18}$ (25 cm × 2.1 mm) column. The test sample is introduced to the head of the separation column using a Rheodyne injector valve which contains a 5 ul sample loop.

After HPLC, the effluent comprising the analyte of interest (nitro-PAH) and the mobile phase (solvent) are directed into the interface 12 of FIG. 2 described previously. The interface is heated by an insulated Nichrome wire coil and a thermocouple held in place between the heating coils and the inlet tube monitors the internal temperature. The interface is maintained at 300° C. uniformly for this nitro-PAH analysis. The expansion chamber, the solvent gas collection tubes, and the analyte gas collection tube are maintained uniformly at a reduced pressure of 100–1000 micron by a vacuum pump. The heating of the analyte and the solvent in admixture results in the formation of a wet aerosol.

After entering the expansion chamber, the wet aerosol undergoes adiabatic expansion and further heating to form a dry gaseous mixture. Since the gas molecules of solvent are substantially lighter in molecular weight (50 daltons) than the gas molecules comprising the analyte of interest (120–300 daltons) and because the expansion chamber is under reduced pressure, the gaseous molecules of solvent become directed toward the internal periphery of the expansion chamber and are collected by the solvent gas collection tubes positioned at the periphery of the expansion chamber. Concomitantly, the gaseous molecules comprising the analyte (being substantially heavier in molecular weight in comparison to the solvent) migrate substantially towards the internal center of the expansion chamber and are collected by the analyte gas collection tube under vacuum pressure. Chemical evaluation of the gaseous molecules collected by the analyte collection tubes demonstrates that not less than 98% of the analyte of interest has been separated from the mobile phase solvent in comparison to the liquid admixture which was first introduced into the interface for separation.

The separated analyte of interest then follows the sequence shown by FIG. 4 for detection and measurement. Initially, the separated gaseous molecules comprising the analyte of interest enter the pyrolyzer chamber maintained at 800° C. Pyrolysis products comprise the nitrosyl radical as well as fragments of the parent polycyclic aromatic hydrocarbons. Fragments from the nitro-PAH and such solvent molecules as are present are effectively removed using a cold trap comprising ethylene glycol-water (50-50)/dry ice held at −45° C. The nitrosyl radical, having sufficient vapor pressure in comparison to other compounds, bubbles through the cold trap and proceeds to the detector reaction chamber. The detector reaction chamber is at approximately 1000 micron reduced pressure. Within this reaction chamber, the nitrosyl radical reacts with ozone to yield electronically excited nitrogen dioxide in the following conventionally known reaction sequence.

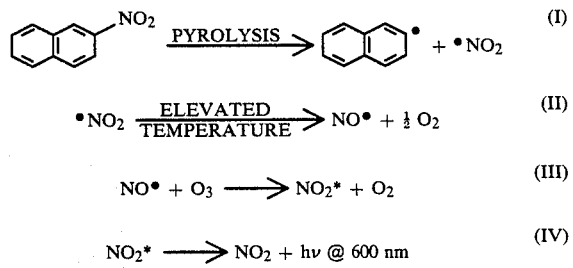

The excited nitrogen dioxide decays back to an unexcited ground state and emits energy which is detected by a photomultiplier assembly. The detector is molar responding, i.e., it will detect the number of moles of excited $NO_2$ per mole of compound such that each mole of $NO_2$ detected corresponds to the number of $NO_2$ molecules on the parent PAH. A representative chromatographic profile of detected nitro-PAH identified as a function of time is illustrated in FIG. 5. The detection limits of this chemiluminescent detection system as described herein are about 1–5 picogrm per compound tested. The profile illustrated by FIG. 5 demonstrates that the interface of the present invention does not interfere with the detector's general response and provides detection limits which are on the order of those obtainable by conventional gas chromatography/chemiluminscent detection systems while maintaining the selectivity of the detector. In comparison, if the interface comprising the present invention is not employed, the best available detection of nitro-PAH is 50-100 nanogram of compound injected using identical HPLC and chemiluminescent detector systems.

The present invention is not to be restricted in form nor limited by the scope except by the claims appended hereto.

What we claim is:

1. An interface useful for separating an analyte of interest from an admixture with a liquid solvent, said interface comprising:
   conduit means for conveying a liquid admixture comprising an analyte of interest and a liquid solvent;
   heating means for vaporizing a liquid admixture comprising an analyte of interest and a liquid solvent into a dry gaseous mixture comprising gaseous molecules of solvent and gaseous molecules of the analyte of interest;
   an adiabatic expansion chamber without internal mechanical means for moving a liquid admixture, said adiabatic expansion chamber being adjacent to and in communication with said heating means and being under reduced pressure for adiabatic expansion and separation of a dry gaseous mixture whereby gaseous molecules of solvent of the gaseous mixture migrate substantially toward the internal periphery of said adiabatic expansion chamber and gaseous molecules of the analyte of interest of the gaseous mixture migrate substantially toward the internal center of said adiabatic expansion chamber;
   solvent gas collection means at the internal periphery of said adiabatic expansion chamber for collection of separated gaseous molecules of solvent; and
   analyte gas collection means at about the internal center of said adiabatic expansion chamber for collection of separated gaseous molecules of the analyte of interest.

2. An interface useful for separating an analyte of interest from an admixture with a liquid solvent, said interface comprising:
   conduit means for conveying a liquid admixture comprising an analyte of interest and a liquid solvent;
   means for vaporizing a liquid admixture comprising an analyte of interest and a liquid solvent into a wet aerosol;
   heating means for converting a wet aerosol comprising an analyte of interest and a solvent into a dry gaseous mixture comprising gaseous molecules of solvent and gaseous molecules of the analyte of interest;
   an adiabatic expansion chamber without internal mechanical means for moving a liquid admixture, said adiabatic expansion chamber being adjacent to and in communication with said means for vaporizing and said heating means and being under reduced pressure for adiabatic expansion and separation of a dry gaseous mixture whereby gaseous molecules of solvent of the gaseous mixture migrate substantially toward the internal periphery of said adiabatic expansion chamber and gaseous molecules of the analyte of interest of the gaseous mixture migrate substantially toward the internal center of said adiabatic expansion chamber;
   solvent gas collection means at the intenal periphery of said adiabatic expansion chamber for collection of separated gaseous molecules of solvent; and
   analyte gas collection means at about the internal center of said adiabatic expansion chamber for collection of separated gaseous molecules of the analyte of interest.

3. The interface as recited in claim 1 or 2 wherein said means for vaporizing comprises heat.

4. The interface as recited in claim 1 or 2 wherein said vaporizing means comprises means for heating the liquid admixture to a temperature ranging from 100°-700° C.

5. The interface as recited in claim 1 or 2 wherein said expansion chamber is under a reduced pressure ranging from 1-1000 microns of mercury.

6. The interface as recited in claim 1 or 2 wherein said solvent gas collection means comprises a gas collection tube under reduced pressure.

7. The interface as recited in claim 1 or 2 wherein said vaporing means comprises an inlet tube having a beveled nozzle.

8. The interface as recited in claim 1 or 2 further comprising at least one solvent retaining chamber in fluid communication with said solvent gas collection means.

9. The interface as recited in claim 1 or 2 further comprising a liquid chromatography system in fluid communication with said interface.

10. The interface as recited in claim 1 or 2 further comprising a high pressure liquid chromatography system in fluid communication with said interface.

11. The interface as recited in claim 1 or 2 further comprising a gas chromatography detection system in fluid communication with said interface.

12. The interface as recited in claim 1 or 2 wherein said analyte gas collection means comprises a gas collection tube under reduced pressure.

13. The interface as recited in claim 12 wherein said analyte gas collection tube comprises an analyte collection tube having a beveled nozzle.

14. The interface as recited in claim 1 or 2 further comprising a detector in fluid communication with said interface.

15. The interface as recited in claim 14 wherein said detector is selected from the group consisting of chemiluminescent detectors, thermal conductivity detectors, flame ionization detectors, thermionic emission detectors, flame photometric detectors, electron capture detectors, helium detectors and photoionization detectors.

16. The interface as recited in claim 2 wherein said means for converting the wet aerosol into a dry gaseous mixture includes heating means.

* * * * *